United States Patent
Kawagishi et al.

(10) Patent No.: US 6,635,018 B2
(45) Date of Patent: Oct. 21, 2003

(54) ULTRASONIC DIAGNOSIS APPARATUS

(75) Inventors: Tetsuya Kawagishi, Kuroiso (JP);
Naohisa Kamiyama, Otawara (JP);
Yoshitaka Mine, Tochigi (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/861,719

(22) Filed: May 22, 2001

(65) Prior Publication Data

US 2002/0022780 A1 Feb. 21, 2002

(30) Foreign Application Priority Data

May 22, 2000 (JP) ........................... P2000-150396

(51) Int. Cl.⁷ ............................... A61B 8/02
(52) U.S. Cl. ................. 600/447; 600/443; 600/444; 600/472
(58) Field of Search ................. 600/447, 458, 600/444, 445, 437, 472

(56) References Cited

U.S. PATENT DOCUMENTS

| | | | |
|---|---|---|---|
| 5,549,111 A | * 8/1996 | Wright et al. | 600/443 |
| 5,694,937 A | 12/1997 | Kamiyama | |
| 5,724,976 A | * 3/1998 | Mine et al. | 600/458 |
| 5,797,846 A | * 8/1998 | Seyed-Bolorforosh et al. | 600/447 |
| 5,873,830 A | * 2/1999 | Hossack et al. | 600/447 |
| 5,891,038 A | * 4/1999 | Seyed-Bolorforosh et al. | 600/447 |
| 6,042,546 A | * 3/2000 | Bae | 600/447 |
| 6,224,556 B1 | * 5/2001 | Schwartz et al. | 600/447 |
| 6,363,033 B1 | * 3/2002 | Cole et al. | 367/138 |
| 6,436,047 B1 | * 8/2002 | Ramamurthy et al. | 600/447 |

FOREIGN PATENT DOCUMENTS

JP      62-11602      3/1987

* cited by examiner

Primary Examiner—Francis J. Jaworski
Assistant Examiner—William Jung
(74) Attorney, Agent, or Firm—Oblon, Spivak, McClelland, Maier & Neustadt, P.C.

(57) ABSTRACT

An ultrasonic diagnosis apparatus sets transmission conditions that are different depending on a scanning direction so that a transmission sound field in a scanning region is uniform in a scanning of ultrasonic beams in one frame; transmits ultrasonic beams to a subject under the thus set transmission conditions; and samples a harmonics component from a ultrasonic echo signal reflected from a subject of the thus transmitted ultrasonic beams, thereby obtaining a harmonics ultrasonic image of the subject. According to this ultrasonic diagnosis apparatus, in the case of harmonics imaging as well, an entirely uniform image quality with less non-uniformity is achieved, and information useful for diagnosis can be provided on a clinical application site.

16 Claims, 16 Drawing Sheets

FREQUENCY DISTRIBUTION OF
TRANSMISSION ULTRASONIC WAVES

ULTRASONIC DIAGNOSIS APPARATUS

BACKGROUND OF THE INVENTION

1. Field of the Invention

The present invention pertains to an ultrasonic diagnosis apparatus. More particularly, the present invention relates to an ultrasonic diagnosis apparatus for, when ultrasonic beams are scanning in a living body, setting optimal transmission conditions for such each scanning line, achieving a uniform image quality over an image, and providing effective information for analysis on an application site.

2. Description of Related Art

An ultrasonic diagnosis apparatus for obtaining an image signal by transmitting and receiving an ultrasonic signal to/from a subject is used in a variety of modes utilizing noninvasive properties of such an ultrasonic signal. This ultrasonic diagnosis apparatus is mainly of type acquiring a tomographic image of soft tissues of a living body using an ultrasonic pulse reflection technique. There is a variety of imaging techniques based on this ultrasonic pulse reflection technique. In recent years, as one of such techniques, there has been paid special attention to a technique called "harmonic imaging" for imaging a high harmonics component that is a non-basic component in an ultrasonic echo signal.

The harmonic imaging includes a technique called THI (Tissue Harmonic Imaging) for sampling and imaging a high harmonics component caused by distortion of waveforms of such ultrasonic pulses while ultrasonic pulses propagates a living organ; and a technique (hereinafter, referred to as a "contrast echo") using a contrast echo technique for sampling and imaging a contrast medium-derived high harmonics component caused by the fact that micro-bubbles (very small air bubbles) such as levobist being a main component of the contrast medium are stronger in acoustic non-linearity than a living organ, and generates many more high harmonics components.

In the case of the THI, a signal of such high harmonics component is not directly transmitted from a transducer, and is generated by the transmitted ultrasonic pulses propagating from the oscillator by a proper distance. Thus, multiple echoes from an obstacle located immediately beneath the vibrator (for example, ribs when a circulatory region is scanned from a site between ribs) are significantly reduced. In addition, more high harmonics components are generated at a site at which a sound pressure is high. Thus, the beam in a focus direction, i.e., a main lobe is enhanced, and conversely, a side lobe is reduced. As a result, a profile of a sound field beam with its excellent directivity is formed. Therefore, according to a THI having such characteristics, there is provided an advantage that a noise due to multiple reflection or side lobe artifact is reduced, and thus, an image quality is improved, and, for example, the boundary of organs and contrast ratio are improved.

On the other hand, in the case of the contrast echo, a nonlinear component relevant to a basic transmission frequency, in particular, a reflection echo signal of a secondary harmonics component, is detected, and signal levels are discriminated between organs where harmonics are hardly generated. For example, a reflection echo signal includes a basic frequency component of a transmission pulse wave and a harmonics component caused by micro-bubbles that is a main component of contrast medium. Thus, by sampling only such harmonics component from the reflection echo signal, a signal ratio of a contrast medium echo signal to a living organ echo signal is remarkably improved, and an image including a harmonics component, i.e., degree of enhancement caused by contrast medium can be obtained. Therefore, according to a contrast echo having such characteristics, the presence or absence of contrast medium in a region of interest, i.e., a blood flow perfusion or the like, can be observed merely by administrating a comparatively small amount of contrast medium, and information useful for diagnosis is obtained.

In the case of harmonics imaging such as the described THI or contrast echo, the following inconveniences have occurred as compared with a vase of imaging caused by general B mode scanning.

In general, in a sector probe generally used in examination of circulatory organs using an ultrasonic diagnosis apparatus, transmission conditions are identical in scanning lines, each of which configures an image. If a beam deflection angle is greater, the following phenomenon that a transmission sound field differs depending on scanning lines occurs because: 1) a sound pressure of transmission beams formed on scanning lines is reduced; and 2) a beam width increases as compared with a case in which transmission beams are not deflected, and spatial resolution is degraded. Thus, in a conventional B mode scan of ultrasonic beam, in order to take countermeasures against the phenomenon, there is employed a technique for adjusting an image quality such as a receiving gain every scanning line from a receive signal from a non-uniform transmission sound field, thereby generating more uniform images.

However, such countermeasures assume a case of a general B mode image, failing to assume a case of harmonics imaging such as THI or contrast echo.

That is, in harmonics imaging, a transmission sound field, in particular, a sound pressure becomes an important factor relevant to sensitivity, and there is a limitation to compensating for non-uniformity of a transmission sound field by adjustment of a received image quality. Thus, the uniformity of the transmission sound field is required for fully achieving these advantageous effects. The intensity of the harmonics component is proportional to a square of the sound pressure, and thus, a receiving gain having a square in amplitude must be corrected as compared with a conventional B mode. A change in such receiving gain causes a change in noise level, thereby producing a non-uniform image with its different noise level in image.

In harmonics imaging, such tendency is more significant in the case of a contrast echo utilizing micro-bubbles (for example, levobist) that is a contrast medium. That is, in the case of THI, even if the transmission sound pressure is low, although the receiving gain is increased concurrently, whereby a noise component increases in proportional to such increase, sampling/correction of a high harmonics component is possible. In contrast, in the case of contrast echo, if the transmission sound pressure is low, micro-bubbles to be detected may not make a nonlinear response. In such a circumstance, even if the receiving gain is increased to the maximum, it is difficult to detect a micro-bubble derived high harmonics component.

In addition, the beam width generally increases as the transmission beam deflection angle increases irrespective of whether or not harmonics imaging is carried out. With respect to this phenomenon, the non-uniformity of spatial resolution occurs. In particular, in the case of parallel, simultaneous receiving, there is a possibility that a phenomenon such as beam curving is increased.

The foregoing problems apply to another probe such as linear probe as well as sector probe. That is, these problems apply to all the probes that undergo scanning under the same transmission conditions, although actual transmission sound fields are different from each other relevant to a respective one of the scanning lines in order to form the same transmission beams.

SUMMARY OF THE INVENTION

The present invention has been made in view of the foregoing conventional problems. It is a primary object of the present invention to provide an ultrasonic diagnosis apparatus for scanning the inside of a living body by using electronic scanning, and generating and displaying an image, wherein an entirely uniform image quality with its less non-uniformity is achieved, and more useful information is provided by diagnosis at a clinical application site.

It is another object to achieve an entirely uniform image quality with its less non-uniformity, and to provide more effective information for diagnosis at a clinical application site in the case of harmonics imaging such as THI or contrast echo as well.

In order to achieve the foregoing objects, according to the present invention, there is provided an ultrasonic diagnosis apparatus comprising: a transmission condition controller configured to set transmission conditions that are difference according to a scanning direction of ultrasonic beams so as to correct non-uniformity of a transmission sound field for each scanning region in scanning of the ultrasonic beams; a ultrasonic transmitter configured to transmit the ultrasonic beams to a subject under the transmission conditions set by the transmission condition controller; and an image generator configured to obtain a ultrasonic image of the subject from a ultrasonic echo signal reflected from the subject of the ultrasonic beams transmitted by the ultrasonic transmitter.

In the present invention, the ultrasonic transmitter can be configured to change the transmission conditions in one image mode.

In the present invention, the transmission conditions can be at least one of a transmission aperture, a transmission aperture area, a transmission aperture position, a transmission aperture shape, a transmission sound pressure, a transmission pulse wave form, a frequency distribution condition for transmission ultrasonic wave, a focus, a transmission element distribution, and a transmission aperture weighting function.

In the present invention, the transmission condition controller can be a controller configured to set the transmission sound pressure or MI (Mechanism Index) value in the scanning region to be uniform or setting the transmission sound pressure or MI value in a virtual face vertical to the scanning line to be uniform.

In the present invention, the image generator can comprise a measure configured to measure an index concerning a transmission sound field for such each scanning direction from the ultrasonic echo signal. The average intensity of echo signals on scanning lines each or its center frequency is exemplified for the index concerning the transmission sound field.

In the present invention, the image generator can comprise a display configured to display the index measured by the measure.

In the present invention, the transmission condition controller can comprise a controller configured to set the transmission condition based on the index measured by the measure.

In the present invention, the transmission condition controller can comprise a controller configured to enable an operator to set the transmission conditions.

In the present invention, the ultrasonic transmitter can comprise a pulsar in number that is smaller than the number of transmission scanning lines along the scanning direction and a transmitter for transmitting ultrasonic waves under transmission conditions different depending on each direction of the scanning while such each pulsar is switched.

In the present invention, a controller configured to change receiving conditions for such each scanning direction can be further provided.

In the present invention, a generator configured to generate an image by a plurality of transmissions relevant to the scanning direction can be further provided.

According to another aspect of the present invention, there is provided an ultrasonic diagnosis apparatus comprising: a transmission condition controller configured to set transmission conditions that are different according to a scanning direction of the ultrasonic beams so as to correct non-uniformity of a transmission sound field in a scanning region in scanning of ultrasonic beams in one frame; a ultrasonic transmitter configured to transmit the ultrasonic beams to a subject under transmission conditions set by the transmission condition controller; and an image generator configured to sample a harmonics component from a ultrasonic echo signal reflected from the subject of the ultrasonic beams transmitted by the ultrasonic transmitter, thereby obtaining a harmonic ultrasonic image of the subject.

According to still another aspect of the present invention, there is provided an ultrasonic diagnosis apparatus comprising: a transmission condition controller configured to set transmission conditions that are different according to a scanning direction of the ultrasonic beams based on manual operation of an operator so that a transmission sound field for each scanning region enters a desired state in scanning of ultrasonic beams in one frame; a ultrasonic transmitter configured to transmit the ultrasonic beams under transmission conditions set by the transmission condition controller; and an image generator configured to obtain a ultrasonic image of the subject from a ultrasonic echo signal reflected from the subject of the ultrasonic beams transmitted by the ultrasonic transmitter.

According to still another aspect of the present invention, there is provided an ultrasonic diagnosis apparatus comprising: a transmission condition controller configured to set transmission conditions that are different according to a scanning direction of the ultrasonic beams so as to correct non-uniformity of a transmission sound field for each scanning region in scanning of transmission beams in one frame; a receiving condition corrector configured to correct receiving conditions of the ultrasonic beams according to transmission conditions set by the transmission condition controller; a ultrasonic transmitter configured to transmit the ultrasonic beams to a subject under transmission conditions set by the transmission condition controller; and an image generator configured to obtain a ultrasonic image of the subject under receiving conditions corrected by the receiving condition corrector from a ultrasonic echo signal reflected from the subject of ultrasonic beams transmitted by the ultrasonic transmitter.

In the present invention, the transmission condition controller can have a selector configured to select type of contrast medium and a controller configured to set the transmission conditions according to the contrast medium selected by the selector. The type of contrast medium used here includes levovist, optison, and sonosoid or the like, for example.

According to the present invention, transmission conditions are optimally set according to purposes for each scanning line, and partial image degradation is prevented, thereby generating an image having its uniform image quality. In particular, an image with its high image quality suitable to case of harmonics imaging such as THI or contrast echo can be obtained.

The other configuration and advantageous effects according to the present invention is evident from a description based on the following embodiments and accompanying drawings of the invention.

BRIEF DESCRIPTION OF THE DRAWINGS

In the accompanying drawings,

FIG. 16 is a view illustrating an example of transmission element distribution (sparse distribution), where

DETAILED DESCRIPTION OF PREFERRED EMBODIMENTS

Hereinafter, preferred embodiments of an ultrasonic diagnosis apparatus according to the present invention will be specifically described with reference to the accompanying drawings.

Figure 1:
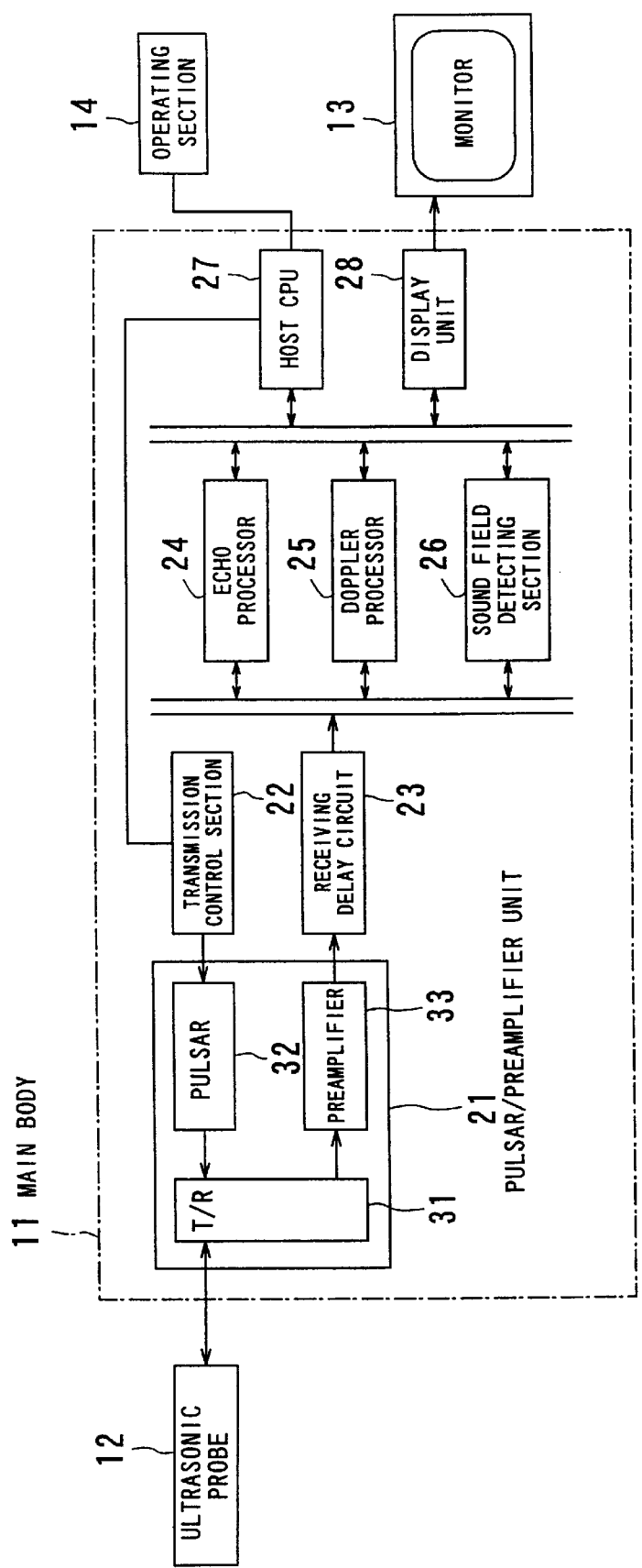
FIG. 1 is a schematic block diagram depicting an ultrasonic diagnosis apparatus according to one of the preferred embodiments of the present invention.

An ultrasonic diagnosis apparatus shown in FIG. 1 comprises: a main body 11; a ultrasonic probe 12 connected this main body 11; a monitor 13, and an operating section 14. The operating section 14 supplies a variety of instructions or information from an operator to the main body 11. This operating section includes, for example, operating switches, keyboard, and pointing devices (such as mouse or trackball) for setting ROI (region of interest), thereby making it possible to select an image mode such as B mode or harmonics mode by operator's manipulation or to set/change ultrasonic beam transmission conditions or the like.

The ultrasonic probe 12 has a piezoelectric oscillator made of ceramics or the like that serves as an electric/mechanical reversible converter element. A plurality of electronic oscillators are arranged in one-dimensional or two-dimensional array manner, and are mounted on a tip end of the probe, whereby one-dimensional array probes or two-dimensional array probes are configured. In this manner, the probe 12 converts a drive voltage supplied from the main body 11 into a ultrasonic pulse signal, and transmits the converted signal in a desired direction inside of a subject, whereas the probe converts a ultrasonic echo signal reflected at a boundary at which an acoustic impedance of the internal tissues of the subject body is different from another or backwardly scattered by a very small scattering element into an echo signal of the corresponding voltage, and delivers the converted signal to the main body 11.

The main body 11, as shown in FIG. 1, comprises: a pulsar/preamplifier unit 21 connected to the probe 12; a transmission control section (transmission controller) 22 placed at the transmission side; a receiving delay circuit 23 placed at the receiving side of the pulsar/preamplifier unit 21; an echo processor 24; a Doppler processor 25; a sound field detecting section 26; and a display unit 27. The main body 11 further comprises a host CPU 28 responsible for receiving operational data from the operating section, the host CPU serving as a nucleus of controlling the entire system including setting of each of the elements or operation control. Although not shown in particular in the present embodiment, the main body 11 includes a cardiac cavity detecting processor and a 3D processor or the like as required.

The transmission control section 22 functionally sets transmission conditions such as a transmission aperture, a transmission aperture area, a transmission aperture position, a transmission aperture shape, a transmission sound pressure, a transmission pulse waveform, a frequency distribution of transmission ultrasonic beams, a focus, and a transmission element distribution so that the transmission sound field in a scanning region formed by scanning lines each of the ultrasonic beams caused by the probe 12 is uniform. Then, this control section delivers to the pulsar/preamplifier unit 21 a control signal of a transmission pulse voltage supplied to each oscillator of the probe under the transmission conditions. This transmission control section 22 can be composed of any of only software components, only hardware components and a combination of these components.

The pulsar/preamplifier unit 21 comprises: a T/R 31 connected to the probe 12; a pulsar (transmitter) 32 placed at the transmission side; and a preamplifier 33 placed at the receiving side of T/R 31.

The pulsar 32 is composed of one circuit set having a function capable of momentarily switching one of a plurality of transmission conditions or a plurality of circuit sets each having a function capable of switching it by a plurality of transmission conditions. This pulsar generates a drive pulse voltage under transmission conditions set at a transmission control section 22, and supplies a drive signal based on this pulse voltage to the probe 12 via T/R 31. In this manner, the direction/convergence of the ultrasonic beams from the probe 12 are controlled in a two-dimensional or three-dimensional manner, and beam forming is carried out under the transmission conditions that are different depending on each scanning line so that the transmission sound field in the scanning region is uniform.

The preamplifier 33 receives from T/R 31 an echo signal of a voltage that corresponds to the ultrasonic echo signal converted by the probe 12, amplifies the received echo signal, and delivers the amplified signal to a receiving delay circuit.

The receiving delay circuit 23 is composed of one circuit set (beam former) or a plurality of circuit sets required for parallel simultaneous receiving. This delay circuit delays and adds echo signals from the preamplifier so as to meet conditions for the direction/convergence of ultrasonic beams caused by beam forming during reception, and delivers the delayed and added signals to an echo processor 24, a Doppler processor 25, and a sound field detecting section 26.

The echo processor 24 detects waves in a quadrature manner at a predetermined reference frequency in response to a receiving signal from the receiving delay circuit 23, and generates a two-dimensional or three-dimensional spatial distribution image according to the signal amplitude of such wave detected signal, whereas it carries out signal processing concerning image generation of harmonics imaging. Here, in the case where an encoded ultrasonic wave other than a conventional ultrasonic pulse is used as transmission ultrasonic beams or in the case where a pulse compression technique is used, de-convolution processing is carried out instead of the quadrature phase wave detection processing. The thus generated image corresponds to two-dimensional or three-dimensional morphological information of a subject. In particular, the image includes information on contrast medium as well as morphological information in the case of using a contrast medium.

The Doppler processor 25 generates two-dimensional or three-dimensional spatial distribution image data such as motion or deviation of tissues of a subject by measuring a time change of the phase in response to a receiving signal from the receiving delay circuit 23. This processor 25 further carries out signal processing concerning PW (pulse Doppler) or CW (continuous wave Doppler).

The sound field detecting section 26 detects an average intensity or the like of echo signals on scanning lines each of ultrasonic beams in response to the receiving signal from the receiving delay circuit 23.

The display unit 27 carries out processing such as logarithmic compression or scan conversion relevant to data from the echo processor 24, Doppler processor 25, and sound field detecting section 26, and displays a predetermined image on a monitor 13.

Now, examples of setting and changing transmission conditions by a transmission control section 22 will be described with reference to FIG. 2 to FIG. 11. Here, a description is given by exemplifying a one-dimensional array probe (sector probe) as a ultrasonic probe 12 in comparison with a conventional case.

Figure 2:
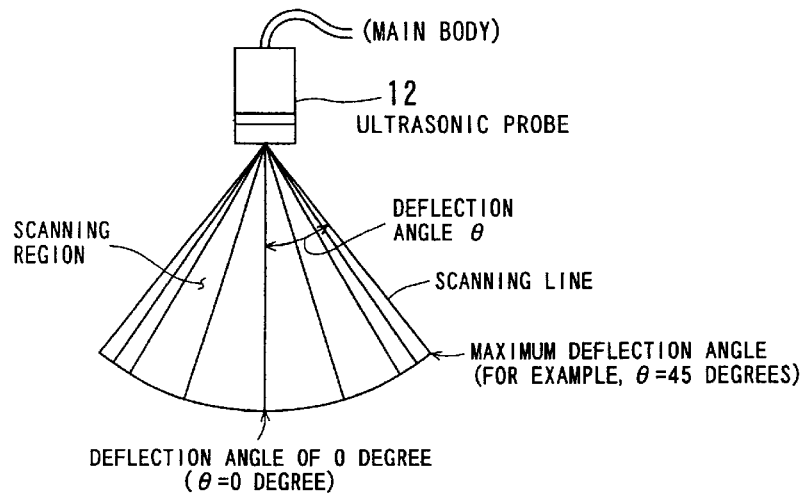
FIG. 2 is a schematic view illustrating a scan region with a sector probe.

FIG. 2 shows a scanning region of ultrasonic beams electronically scanned by the sector probe 12. In FIG. 2, with respect to the ultrasonic beams transmitted from the sector probe 12, electrical scanning is carried out in a sector shaped scanning region formed by a plurality of scanning lines up to a scanning line whose deflection angle is maximal (for example, $\theta=45$ degrees) after deflected at a predetermined angle on both sides while scanning lines are sandwiched when a deflection angle extending in normal direction from the center of a transmission aperture formed by an array oscillator at the tip end of the probe is 0 degree ($\theta=0$ degree).

Figure 3A:
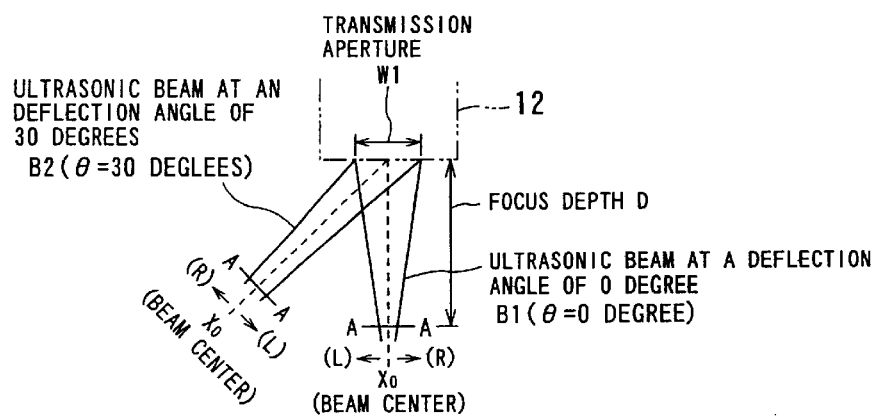
FIG. 3A and FIG. 3B are schematic views each illustrating a profile of main beams at a focus depth under conventional transmission conditions.
Figure 3B:
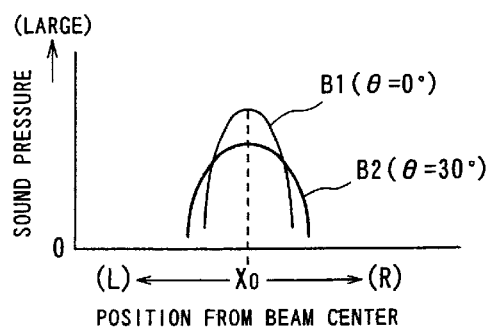

FIG. 3A and FIG. 3B each illustrate a case of the conventional same transmission conditions in beam scanning in a scanning region shown in FIG. 2. FIG. 3A shows an example of transmission conditions (transmission aperture W1 and focus depth D1) for the ultrasonic probe 1. FIG. 3B shows a profile (horizontal axis: a position from the beam center and vertical axis: sound pressure) of schematic main beams at a focus depth D of a respective one of the transmission beam B1 on a scanning line on which the deflection angle shown in FIG. 3A is 0 degree ($\theta=0$ degree) and the transmission beam B2 on a scanning line on which the deflection angle is 300 degrees ($\theta=30$ degrees), respectively.

Figure 4:
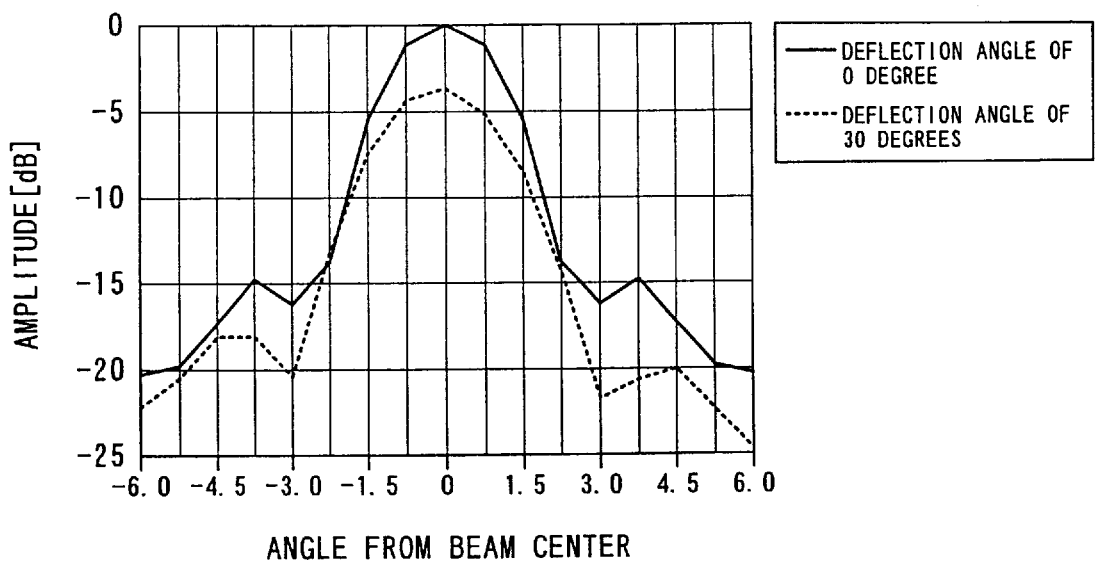
FIG. 4 is a graph depicting a beam profile at a focus depth under the conventional transmission conditions.

FIG. 4 shows the result obtained when a beam profile (horizontal axis: an angle from the beam center and vertical axis: amplitude) at a focus depth D1 between the transmission beam B1 when $\theta=0$ degree and the transmission beam B2 when $\theta=30$ degree under conditions when transmission aperture W1=12.6 mm, focus depth D1=60 mm, and transmission waveforms are pulse waveforms from among transmission conditions shown in FIG. 3A and FIG. 3B by way of actual simulation.

From the result, in the case where the deflection angle is 30 degrees, as compared with a case where the deflection angle is 0 degree, it is verified that the sound pressure of the beam center is reduced, and the beam width increases, whereby it is found that degradation of the transmission sound field occurs.

In the case of the conventional example, transmission conditions are identical between different scanning lines in a scanning region. Thus, a transmission sound field changes between scanning lines due to an element factor or an effect of apparent aperture change or the like. In particular, a difference in transmission sound field is considered to be the greatest between a scanning line in the vicinity of the center at which the deflection angle in the scanning region is small and a scanning line in the vicinity of an edge at which the deflection angle is maximal.

Therefore, the following inconveniences occur at a site where a transmission beam deflection angle is large.

Figure 5:
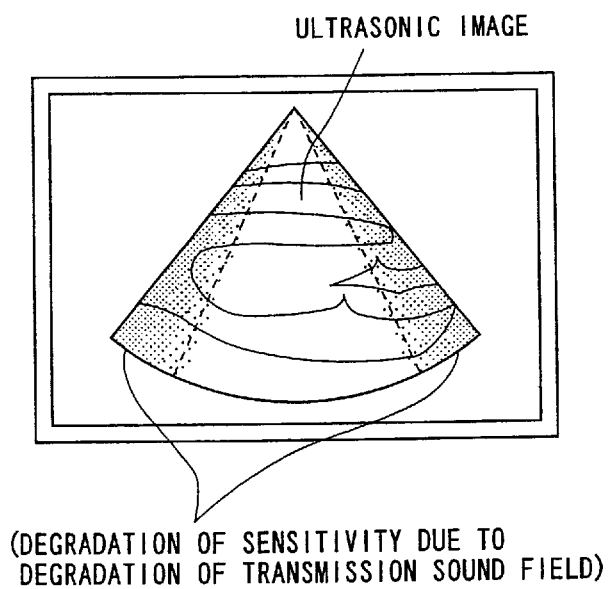
FIG. 5 is a schematic view showing a display example of a harmonics imaging or the like caused by a sector probe.

1) In the case of THI, generation of a harmonics component is lowered, and sensitivity is degraded. Therefore, as shown in FIG. 5, an image on the monitor 13 is darkened, making it difficult to identify a structure of a living body, and a display region for images useful for diagnosis decreases.

2) In the case of a contrast echo carried out using a contrast medium, a sound pressure for exciting microbubbles in the contrast medium component becomes nonuniform. Therefore, as shown in FIG. 5, the image on the monitor is darkened, making it possible to discriminate a loss of dying at a lesion such as blood flow, which is problematic in clinical diagnosis.

3) As a deflection angle increases, the scanning lines and the spatial resolution in vertical direction to each beam are degraded, and further, sensitivity is lowered.

Figure 6:
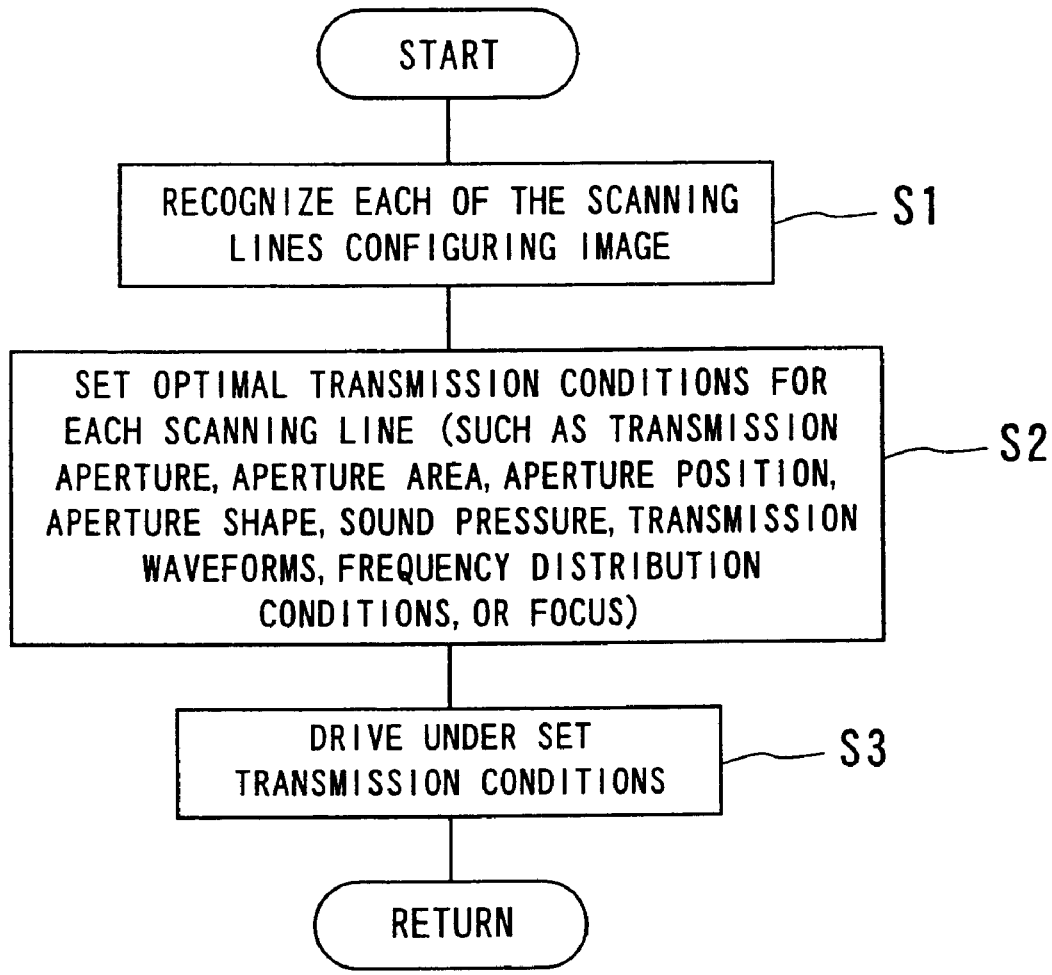
FIG. 6 is a flow chart schematically showing exemplary processing caused by a transmission control section.

In contrast, in the present embodiment, the following operation and advantageous effects can be achieved because the transmission control section 22 carries out processing shown in FIG. 6, whereby scanning lines each configuring an image are recognized (step S1); there are set transmission conditions such as optimal transmission aperture, aperture area, aperture position, aperture shape, sound pressure, transmission waveforms, frequency distribution conditions, focus, or transmission element distribution (step S2); and processing is driven under such transmission conditions (step S3), whereby beam scanning in the scanning region is controlled. Hereinafter, an example of settings and its advantageous effect will be described by transmission conditions.

(Transmission Sound Pressure)

A transmission sound pressure is corrected (set) so that the sound pressures on scanning lines are equal to each other irrespective of whether a transmission beam deflection angle is large or small. This correction is possible in any of a case where the transmission line sound pressure on a scanning line with its large deflection angle is higher than that with its small deflection angle, and conversely, a case where the scanning line transmission sound pressure with its small deflection angle is lower than that with its large deflection angle. This is because, in any case, a relative relationship is similar. An example of settings in the latter case is shown in FIG. 7.

Figure 7:
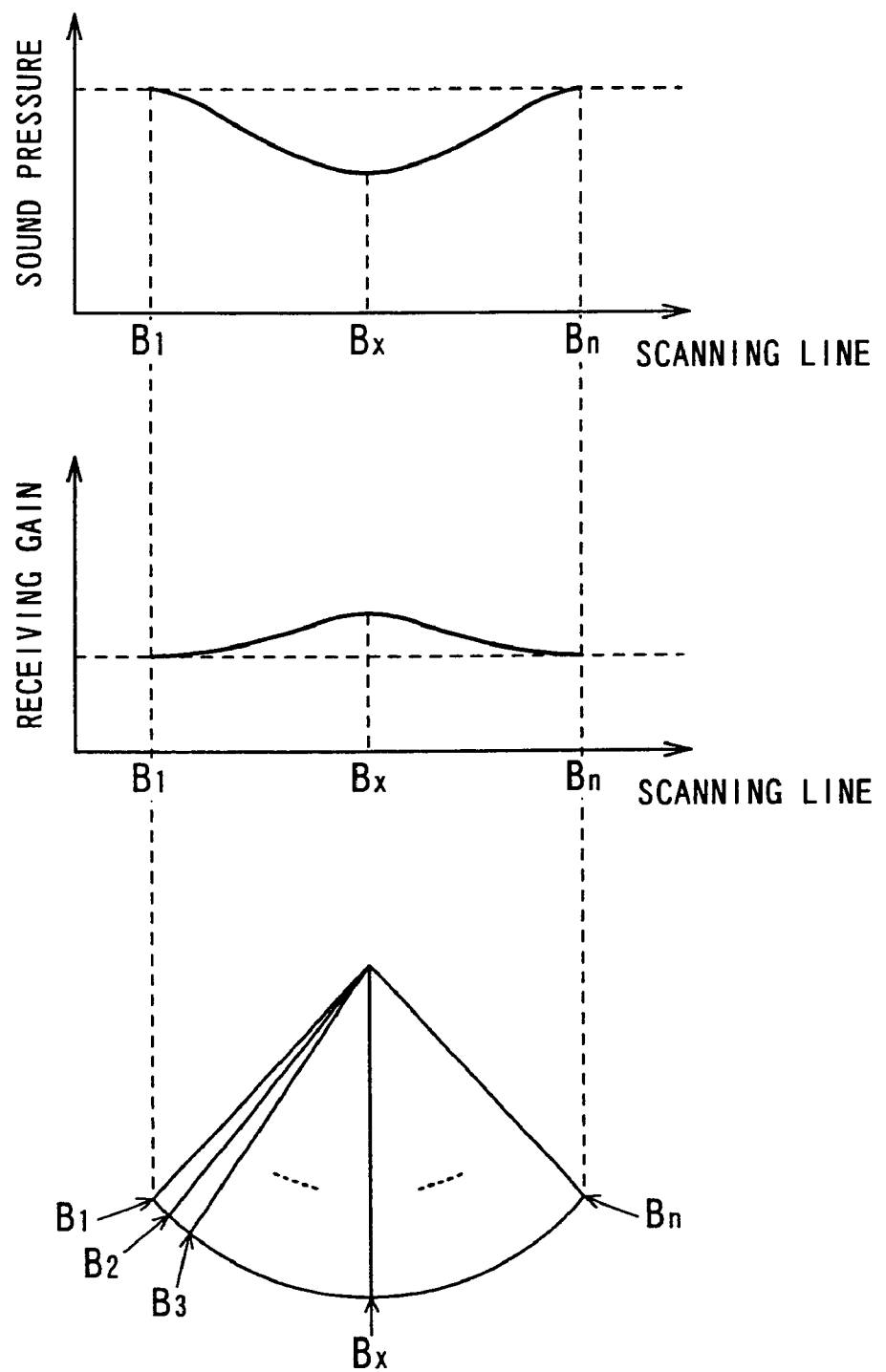
FIG. 7 is a schematic view illustrating an example of setting a sound pressure of transmission beam.

As shown in FIG. 7, the sound pressures of transmission beams on scanning lines B1, B2, B3, . . . , Bx, . . . , Bn (refer to the lower field in FIG. 7) each configuring a sector scan region is set so as to be lowered when the scanning lines B1, Bn each at both ends at which a deflection angle is the greatest are defined as a reference, as the deflection angle is smaller from such reference position, and so as to be the smallest on the scanning line Bx at the center at which the deflection angle is the smallest (refer to upper field in FIG. 7).

In this case, a noise is increased as required in the case where correction cannot be carried out by only sound pressure due to system restriction. Instead, connection to be carried out during transmission can be done by receiving gain control on the scanning lines B1 . . . Bn each (refer to middle field in FIG. 7). That is, in an example shown in FIG. 7, the receiving gain on scanning lines B1 . . . Bn each are set so as to increase when a scanning line Bx at the center at which a deflection angle is the smallest is defined as a reference, as the deflection angle is smaller from this reference position, and so as to be the greatest on each of the scanning lines B1 and Bn at both ends at which the deflection angle is the greatest.

Figure 8:
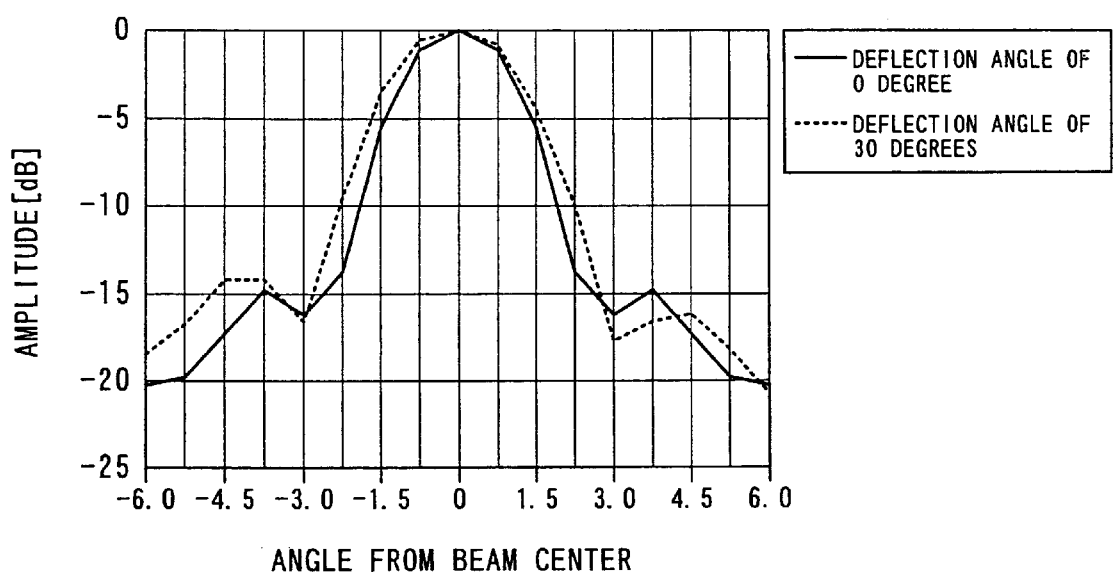
FIG. 8 is a graph depicting a beam profile at a focus depth when the sound pressure of deflection beams is corrected.

FIG. 8 shows the result obtained when correction is carried out so that the sound pressures in the vicinity of the focus between a transmission beam when θ=0 degree and a transmission beam when θ=30 degrees are equal to each other by simulation similar to that described previously under transmission conditions such as transmission aperture W1=12.6 mm, focus depth D1=60 mm, and when the transmission waveforms are pulse waveforms.

In this way, the sound pressures in the vicinity of the focus are set so as to be equal to each other in any position of transmission beams irrespective of a difference in deflection angle, whereby, in particular, a nonlinear response can be expected in the case of imaging using a medial non-linearity such as THI or contrast imaging, which is effective. This is because the amplitude of a receiving signal is proportional to a power, mainly a square of the transmission sound pressure on the ultrasonic beams, and an effect of the transmission sound pressure have serious effect on an image unlike image generation caused by a linear component as in a conventional B mode image.

In the present embodiment, although the sound pressures in the vicinity of focus are compared, in actuality, it is ideal that adjustment is made in consideration of the sound pressure of the entire scanning lines. For example, more uniform sound field design on scanning lines can be made by using an axis focus together (for example, refer to Japanese Patent Application No. 2000-060187).

(Aperture Area)

An aperture area is set so as to be relatively greater as a transmission beam deflection angle is greater. Setting examples are shown in FIG. 9A and FIG. 9B.

Figure 9A:
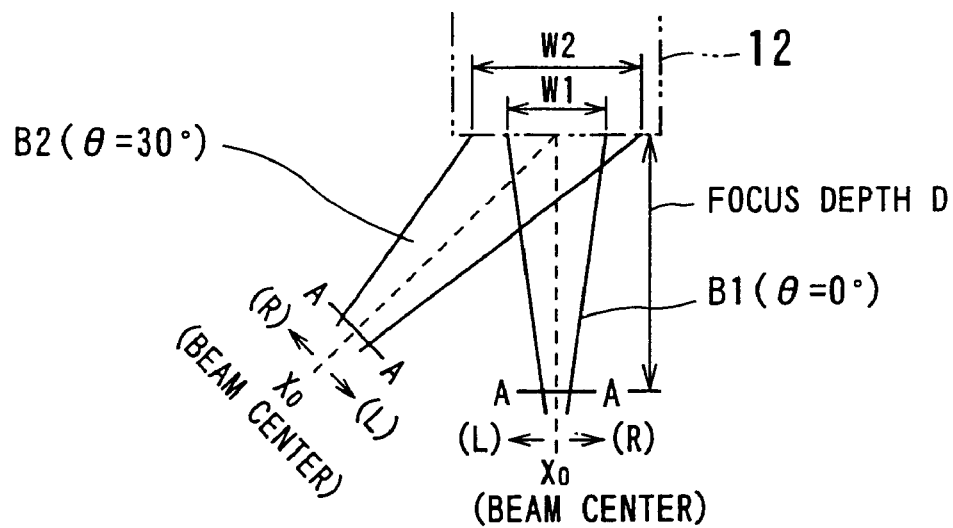
FIG. 9A and FIG. 9B are schematic views each illustrating a beam profile at a focus depth when a transmission aperture is corrected.
Figure 9B:
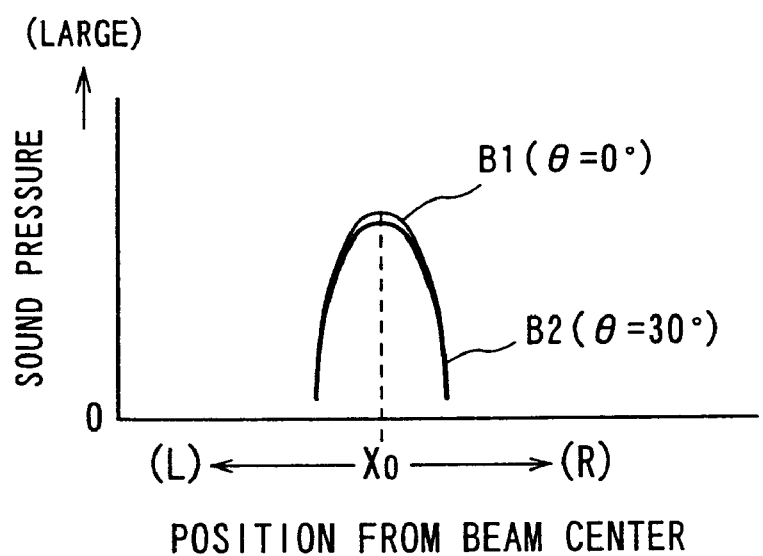

In this case, as shown in FIG. 9A, if a transmission aperture W2 of a transmission beam B2 when θ=30 degrees is greater that a transmission aperture W1 of a transmission beam W1 when θ=0 degree (W1<W2), the sound pressure and beam width at the beam center of a respective one of these transmission beams B1 and B2 are almost equal to those of another one, as shown in a beam profile in the vicinity of the focus shown in FIG. 9B.

Figure 10:
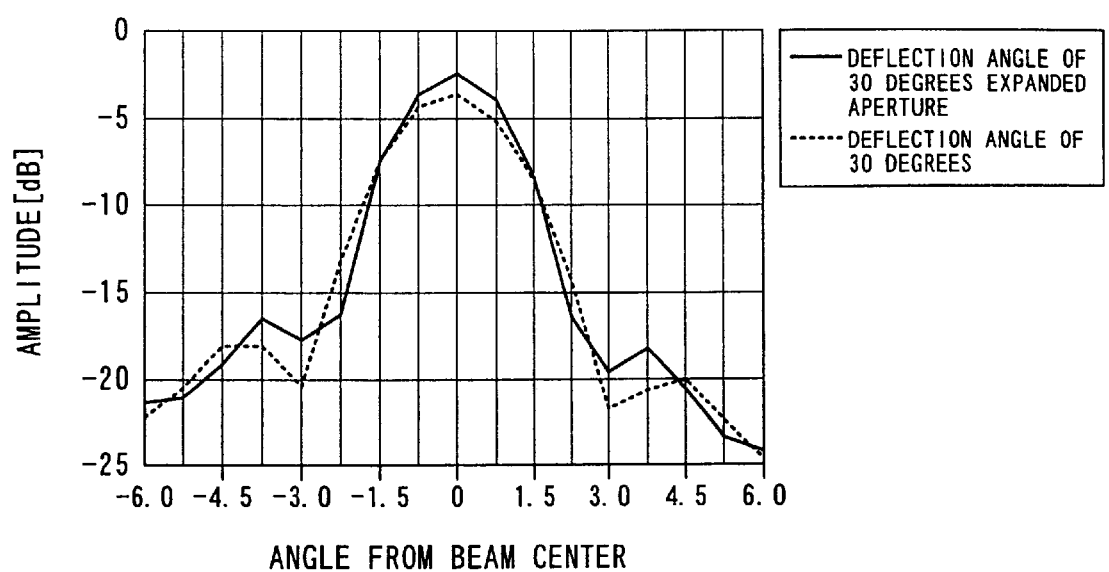
FIG. 10 is a graph depicting a beam profile at a focus depth when a transmission aperture of deflection beams is enlarged.

FIG. 10 shows a beam profile at a focus depth when a transmission aperture is not changed in the same way as conventionally with the transmission beam B2 when θ=30 degrees by way of actual simulation (W1=12.6 mm) and when the transmission aperture is increased (W2=14.7 mm). In FIG. 9, in the case where the transmission aperture is increased, it is verified that the sound pressure at the beam center becomes high, and the beam width decreases.

Therefore, the aperture area for a deflected transmission beam is set as described above, whereby the shape of the beam can be adjusted. Thus, sensitivity and spatial resolution can be adjusted altogether, whereby a difference in spatial resolution due to deflection can be corrected.

(Transmission Weighting)

In the case of carrying out transmission weighting, a weighting function may be changed for each scanning line. If a transversely symmetrical weighting is applied to a scanning line at a transmission aperture (probe), thereby deflecting the beam, the shape of the transmission beam is not transversely symmetrical, and thus, correction of such beam is carried out. Weighting functions Hamming, Hanning, Blackman, Sink, Gauss or the like can be exemplified.

This transmission weighting plays an important role in that an image quality in scanning direction (depth direction) is uniform in contrast echo. Hereinafter, this fact will be described with reference to FIG. 11 to FIG. 13.

Figure 11:
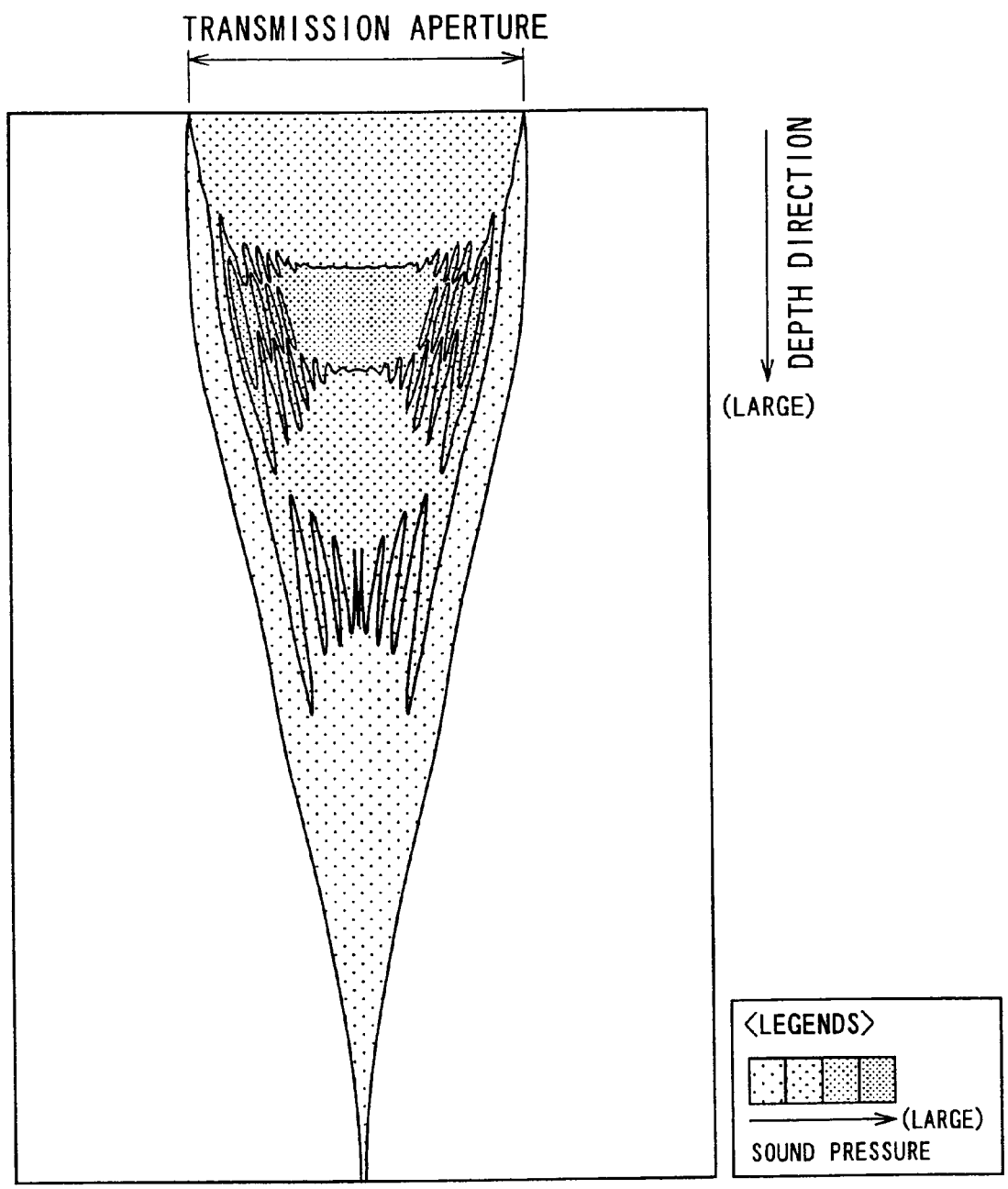
FIG. 11 is a view illustrating the result of beam simulation (prior art) on a scanning face when a transmission weighting is not applied.

FIG. 11 illustrates the result of beam simulation on a basic wave scanning face of ultrasonic beams when a transmission weight is not applied. The conditions used in this simulations are center frequency=2.0 [MHz], sound source pressure=1.0 [MPa], lens focus=5.0 [cm], scan focus=16.0 [cm], maximum display depth=20.0 [cm], and display region (horizontal)=12.8 [cm]. The amplitude is displayed to be specified by the maximum value. In FIG. 11, a ultrasonic beam transmission scanning line is positioned at the center of an image.

According to the result of beam simulation shown in FIG. 11, it is verified that the beam width is large in short distance, and a peak may be generated at a position other than that on the transmission scanning line. In such a circumstance, it is expected that clinical problems as described in the Description of Related Art section will occur.

Figure 12:
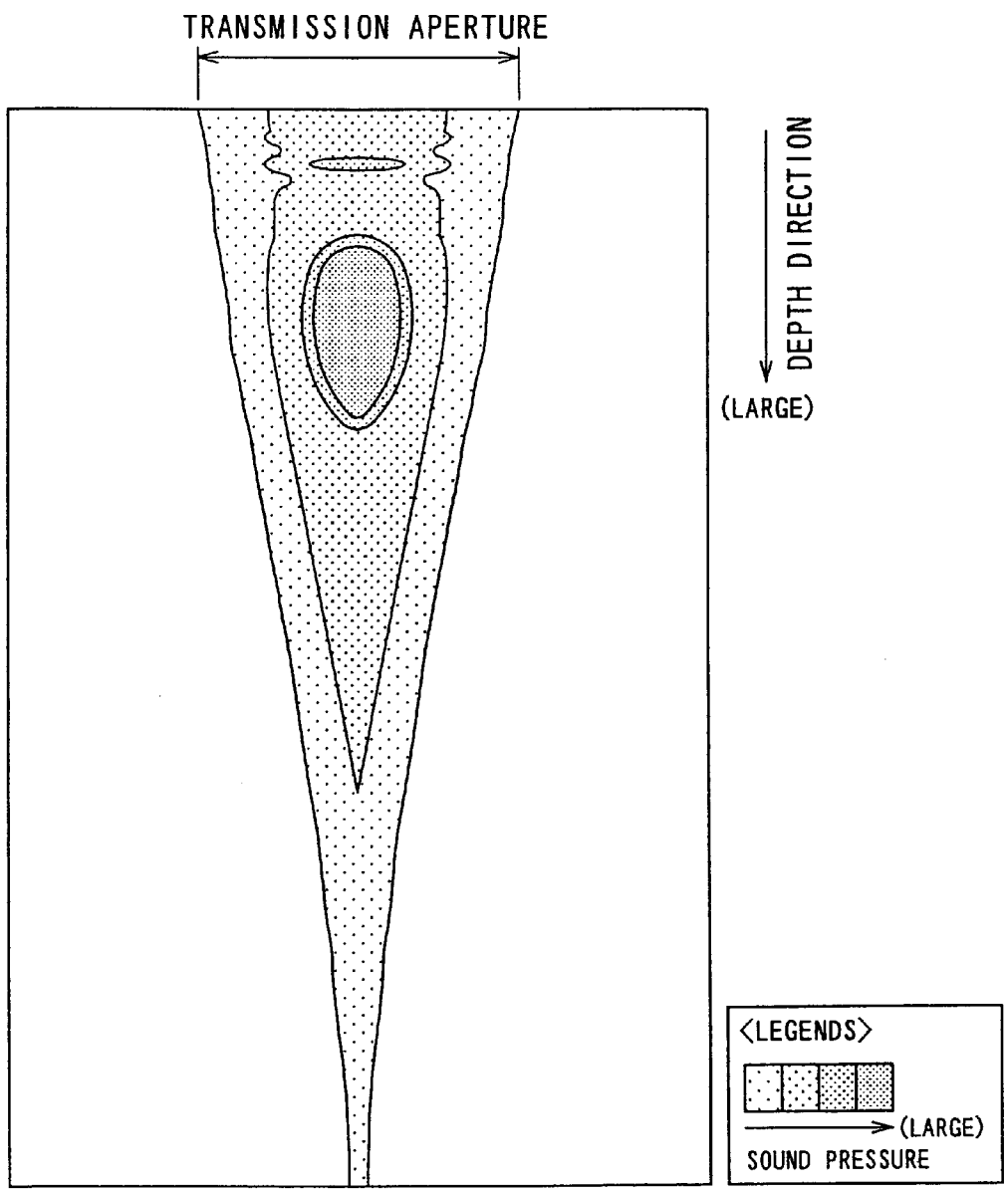
FIG. 12 is a view illustrating the result of beam simulation on a scanning face when a transmission weighting is applied.

FIG. 12 illustrates the result obtained when beam simulation is carried out on a basic wave scanning face when a transmission weighting is applied by a Hamming function. The conditions used in this simulation are similar to those in FIG. 11 described previously. The aperture is set so that a charge energy is almost similar to that in FIG. 11 described previously.

According to the result of beam simulation shown in FIG. 12, it is verified that the beam width in short distance is improved, and a peak of a sound pressure is generated on a scanning line. In the thus beam shape, an effect on contrast medium on a proximal scanning line is reduced. In particular, it can be expected that a contrast enhancement effect is improved in short distance with high scanning line density.

Figure 13:
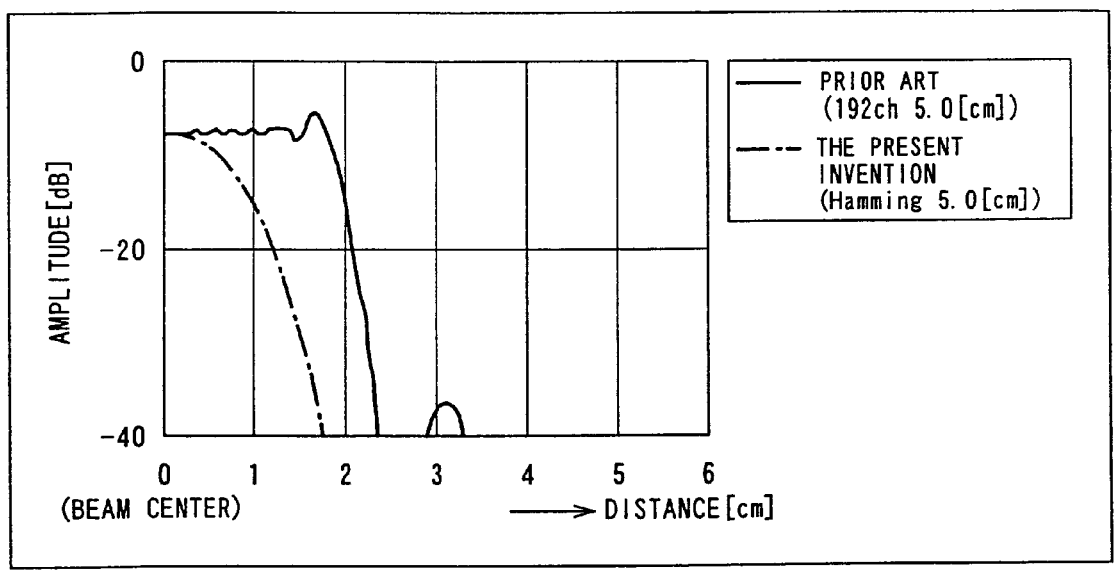
FIG. 13 is a view illustrating a one-sided profile on a beam cross section in the case of FIG. 11 and FIG. 12.

FIG. 13 illustrates a one sided profile of the beam cross section at a depth of 5 cm between a case where the transmission weighting is not applied (prior art) and a case where a transmission weighting is applied by using a Hamming function (the present embodiment), where the horizontal axis of this profile defines the center of beam (scanning line) as 0 cm.

According to this profile, it is verified that beams become fine due to an effect of the transmission weighting in the case of the present embodiment, as compared with the case of the prior art. Moreover, in general, although a transmission weighting is said to be effective in reducing a side lobe, in the case of contrast echo used here, it is found that the shape of a more important main lobe is trimmed, i.e., that the edge of the main lobe is removed. Namely, according to the present embodiment, it is possible to prevent collapse of micro-bubbles that exist on the adjacent scanning line and to prevent a loss of dying in short distance. Therefore, in the experiment shown in the present embodiment, it is verified that a contrast enhancement effect is obtained even in short distance, and a uniform dyeing (image quality) in a depth direction is obtained.

(Transmission Waveforms)

With respect to transmission waveforms, as a transmission beam deflection angle increases, the sound pressure decreases, and the sensitivity is lowered. As countermeasures against it, the frequency of the transmission ultrasonic pulse is set to be lowered, as the transmission beam deflection angle increases. An example of this setting is shown in FIG. 14.

Figure 14:
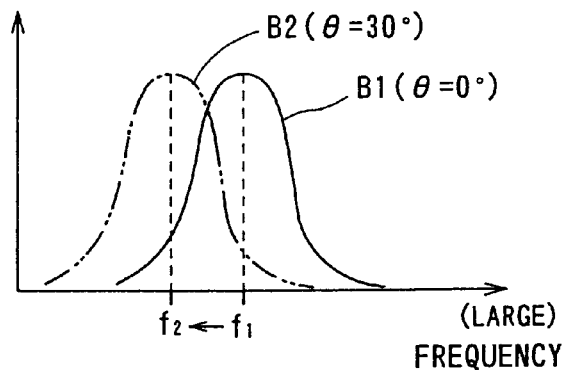
FIG. 14 is a schematic view illustrating a case of correcting a frequency distribution of transmission ultrasonic waves of deflection beams.

In this case, as shown in FIG. 14, when the center frequency f2 of the transmission beam B2 when θ=30 degrees is lowered than the center frequency f1 of the transmission beam B1 when θ=0 degree, penetration of the deflected transmission beam B2 increases, and the transmission sensitivity is relatively improved.

In addition, it is known that micro-bubbles used in a contrast medium responds to a negative sound pressure in particular. Thus, while the negative sound pressure is kept constant, it is expected that the frequency is relatively lowered in deflection beams, thereby the penetration of transmission beams are effectively compensated for.

(Aperture Position)

Figure 15:
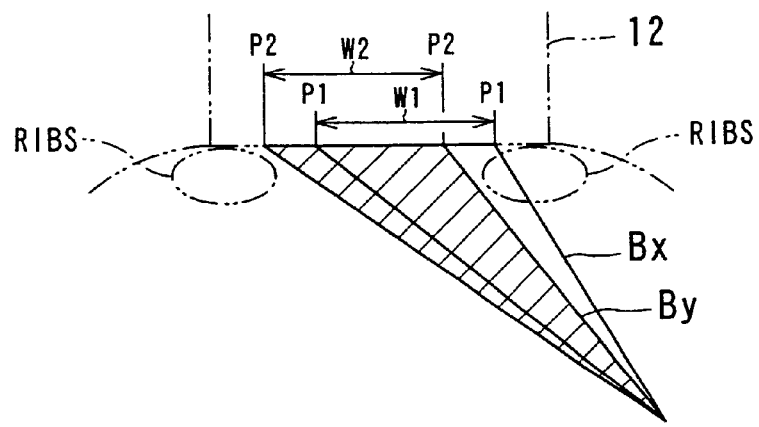
FIG. 15 is a schematic view illustrating a case of setting an aperture position of transmission beams by avoiding the rib portion.

With respect to a transmission aperture position, for example, as shown in FIG. 15, ribs or lungs exist at the periphery in the scanning region of the ultrasonic probe 12. In the case where these ribs or lungs become an obstacle, and the transmission beam Bx is interrupted, which causes lowering of the transmission sensitivity and causes artifacts such as multiple echoes, an aperture position P1 of the transmission beam Bx is set to move to an aperture position P2 in a direction opposite to the deflection direction in the present embodiment.

By using a transmission beam By from this aperture position P2, an effect of ribs can be reduced, and the lowering of transmission sensitivity can be prevented. In addition, it is more effective if the aperture shape as well as aperture position is changed according to a positional relationship in ribs or lungs. This effect is maximized in the case of the field of circulatory organs in particular.

(Transmission Element Distribution)

In conventional ordinary transmission, drive voltages are supplied to all elements (piezoelectric oscillators) in a transmission aperture, and ultrasonic pulses are generated from these elements. Alternatively, in the present embodiment, elements to which a voltage is not supplied is partially set in the transmission aperture. That is, a transmission element is decimated according to a deflection angle, and the distribution density in the transmission aperture is changed. In this way, the distribution density of transmission elements is changed according to the deflection angle, thereby making it possible to control an average transmission sound pressure outputted from the transducer of the ultrasonic probe 12.

The transmission element distribution in the transmission aperture of the ultrasonic probe 12 is called a sparse distribution. This sparse distribution pattern may be regularly distributed in accordance with Gaussian distribution or may be distributed in random. In this manner, an advantageous effect similar to a transmission weighting in which the transmission sound pressure of each of the elements described above is changed at the same time can be achieved by changing the density of the sparse distribution. An example of this sparse distribution (in the case of a one-dimensional array probe) is schematically shown in FIG. 16A and FIG. 16B.

Figure 16A:
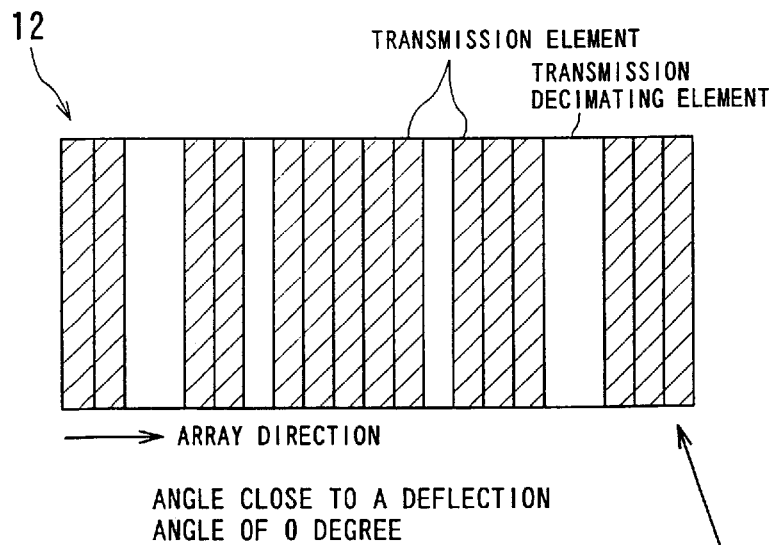
FIG. 16A is a schematic view when a deflection angle is close to 0 degree.
Figure 16B:
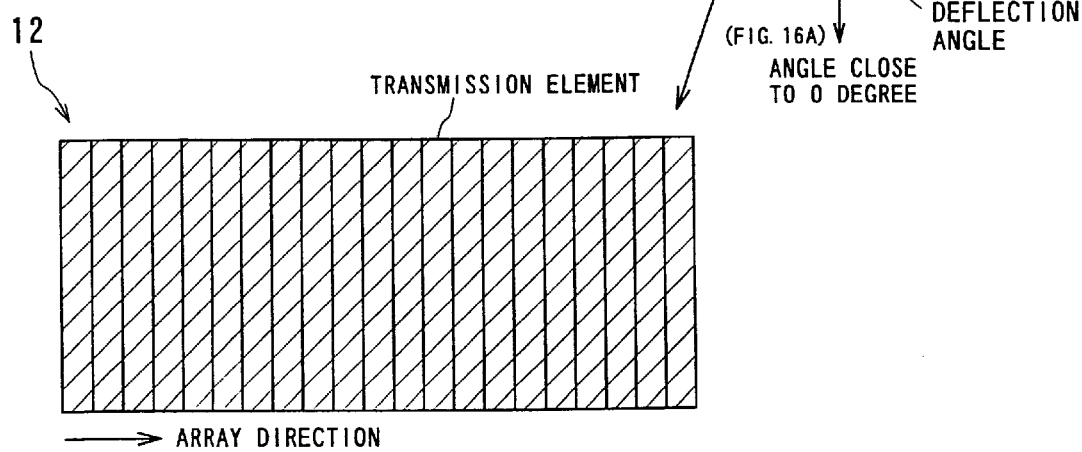
FIG. 16B is a schematic view when a deflection angle is large.

FIG. 16A shows a transmission element distribution (sparse distribution in a one-dimensional array) in the transmission aperture of the ultrasonic probe 12 when the deflection angle is close to 0 degree, and FIG. 16B shows a transmission element distribution (sparse distribution in a one-dimensional array) in the transmission aperture of the ultrasonic probe 12 when the deflection angle is large, respectively. In the case where the deflection angle shown in FIG. 12A is close to 0 degree, as compared with a case where the deflection angle shown in FIG. 12B is large, the density is lowly set by decimating a transmission element. Conversely, in the case where the deflection angle is large, the density is highly set, as compared with a case where the deflection angle is close to 0 degree.

Therefore, there is a possibility that a sound pressure of a pulse is hardly changed in association with the limit and cost or the like on the performance of an analog circuit. In contrast, a technique for changing the transmission element distribution is approximately substituted as described above, whereby only one transmission pulsar will suffice, which is more feasible.

(Aperture Area and Sound Pressure)

Although the transmission conditions (transmission sound pressure, transmission aperture area, transmission waveforms, transmission aperture position, and transmission element distribution) may be changed independently according to scanning lines, they can be changed simultaneously in plurality. An example has shown in FIG. 17.

Figure 17:
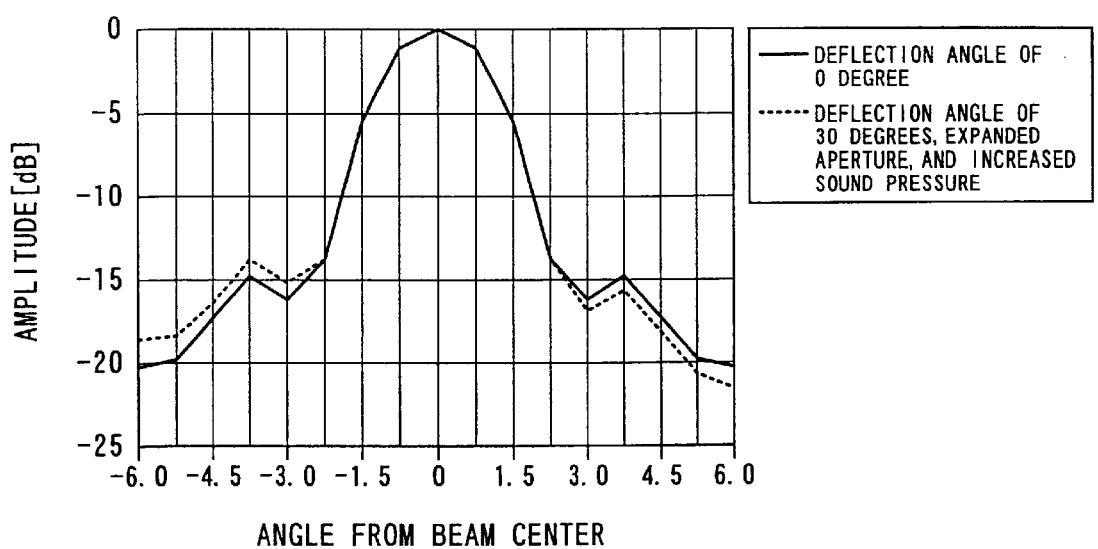
FIG. 17 is a graph depicting a beam profile when a transmission aperture and a sound pressure of deflection beams are corrected at the same time.

FIG. 17 compares a beam profile in the vicinity of a focus when the transmission conditions are set so as to increase a transmission aperture area and increase a transmission sound pressure relevant to deflection beams (for example, θ=30 degrees) with a case of the center beam (θ=0 degree). From this comparison, it is found that the shape of beams that are not deflected relevant to deflection beams is completely equal to a main lobe, in particular. Therefore, it is more effective to change the transmission conditions in plurality than to change them individually.

(Example of Settings Using MI Value)

As a target to be referred to in changing transmission conditions, as described above, apart from the sound pressure of transmission beams or beam profile, an MI value can be used as an index indicative of a transmission sound field by the ultrasonic diagnosis apparatus.

The MI value is an index concerning a mechanical effect on a living body by energy generated when air bubbles formed by expansion are compressed and collapsed when ultrasonic waves propagate physiological tissues, and is a spatial maximum value obtained by dividing a negative peak sound pressure of ultrasonic pulses by a square root of its center frequency. Therefore, the frequency and/or sound pressure can be changed in order to keep the MI value uniform in an image.

As described above, according to the present embodiment, unlike the prior art, the transmission conditions are configured to be optimally set relevant to each scanning line according to purposes instead of performing scanning under predetermined transmission conditions independent of a deflection angle. This makes it possible prevent partial image degradation and to generate an image of more uniform image quality as compared with a conventional example independent of transmission beam orientation. In particular, an image of high image quality can be obtained in THI and contrast echo.

Although the present embodiment has described an example of typical transmission condition settings, the present invention is not limited to this example, and transmission conditions can be variously set without departing from the spirit of the present invention.

In addition, although the present embodiment has described use of a sector probe as a ultrasonic probe, the present invention is not always limited to such use, and transmission conditions can be adjusted or a transmission sound field between scanning lines can be corrected by any other probe in the same way as described above.

Further, although the present embodiment has described a case where transmission conditions are changed for each scanning line, the present invention is not always limited to this case. For example, the distortion of image quality in an image can also be reduced as described above by a method for further dividing the inside of a scanning region forming an image into a plurality of regions composed of a plurality of scanning lines, and adjusting transmission conditions in such each region.

Figure 18:
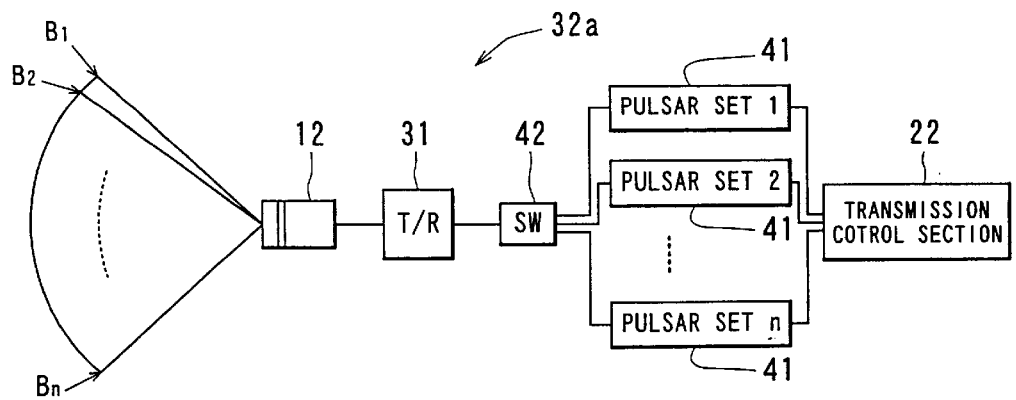
FIG. 18 is a schematic block diagram depicting an exemplary configuration when transmission conditions are switched by pulsar sets in number equal to the number of transmission conditions.

An ultrasonic diagnosis apparatus shown in FIG. 18, apart from a configuration similar to that shown in FIG. 1, comprises: a plurality of pulsars 41 . . . 41 in number equal to the number of transmission conditions as a pulse 32a in a pulsar/preamplifier unit; and a switch (SW) 42 capable of switching each of these pulsars 41 . . . 41. Each of these pulsars 41 . . . 41 is switched for each of the transmission conditions indicated by the transmission control section 22, whereby transmission beams B1 . . . Bn from the ultrasonic probe 12 can be scanned so that the transmission sound field is uniform in a scanning region.

Figure 19:
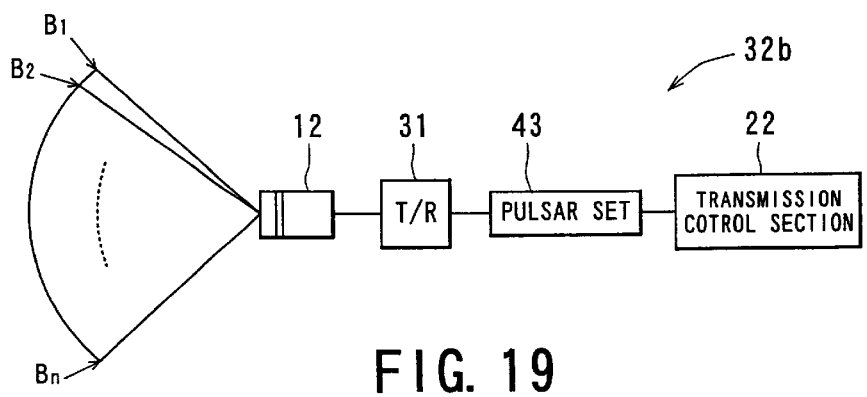
FIG. 19 is a schematic block diagram depicting an exemplary configuration when transmission conditions are switched by one pulsar.

An ultrasonic diagnosis apparatus shown in FIG. 19, apart from a configuration similar to that shown in FIG. 1, comprises: one pulsar 43 capable of switching a plurality of transmission conditions as a pulsar 32b in a pulsar/preamplifier unit at a predetermined velocity. Each of the transmission conditions indicated by the transmission control section 22 is switched by the pulse 3, whereby transmission beams B1 . . . Bn from the ultrasonic probe 12 can be scanned so that the transmission sound field is uniform in a scanning region.

Figure 20:
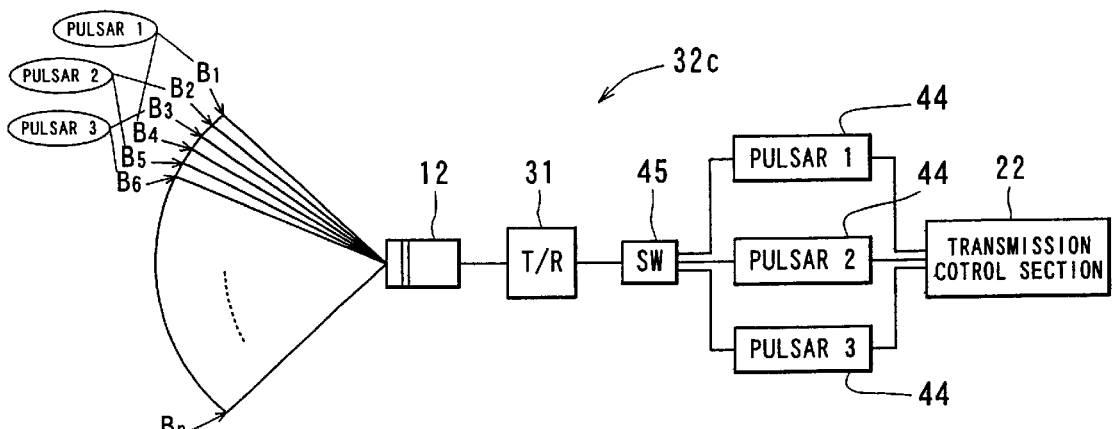
FIG. 20 is a schematic block diagram depicting an exemplary configuration when transmission conditions are sequentially switched by pulsars in number smaller than the number of transmission conditions.

An ultrasonic diagnosis apparatus shown in FIG. 20, apart from a configuration similar to that shown in FIG. 1, comprises: a plurality of pulsars 44 . . . 44 in number smaller than the number of transmission conditions as a pulse 32c in a pulsar/preamplifier unit and a switch (SW) 45 capable of switching each of these pulsars 44 . . . 44. Each of these pulsars 44 . . . 44 is switched in a predetermined pulsar switching mode for each of the transmission conditions indicated by the transmission control section 22, whereby transmission beams B1 . . . Bn from the ultrasonic probe 12 can be scanned so that the transmission sound field is uniform in a scanning region.

In this case, in the pulse switching mode, while one pulse switches transmission conditions, another pulsar carries out transmission. In this way, a transmitting pulsar and a transmission condition changing pulsar are sequentially switched. In this manner, even in the case where a pulsar switching velocity is slower than a rate interval, pulsars in number equal to the number of transmission conditions are not always required. As long as transmission conditions can be switched in a plurality of rate intervals, even pulsars in number smaller than the number of transmission conditions can achieve scanning in the same way as described above.

Figure 21:
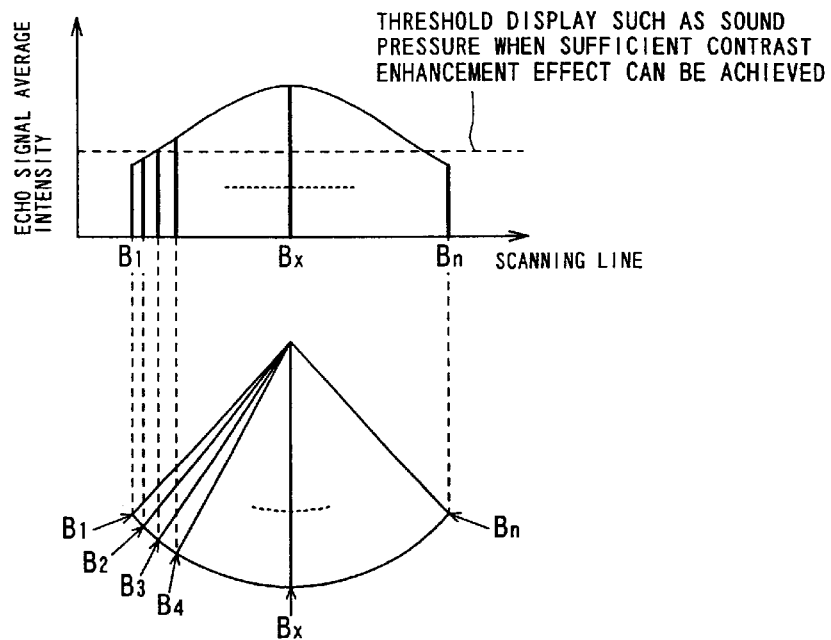
FIG. 21 is a schematic view illustrating a case of monitoring a sound field.
Figure 22:
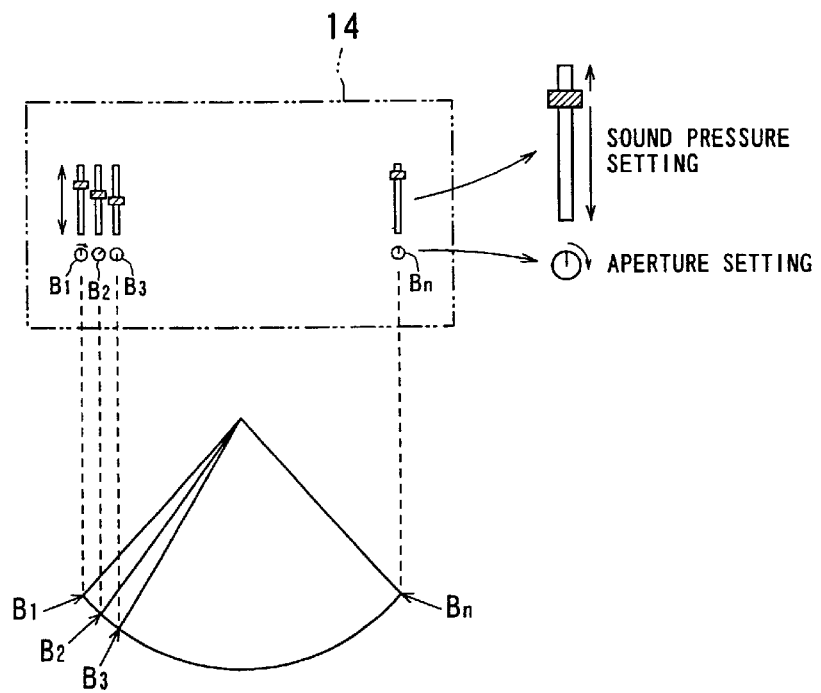
FIG. 22 is a schematic view illustrating a case of an operator setting transmission conditions.

In addition, in the case where the present embodiment is applied to an actual living body, for example, adjustments shown in FIG. 21 and FIG. 22 are possible.

FIG. 21 illustrates a case where a sound field in a living body is monitored. In the described embodiment, in a uniform medial quality, there is provided a configuration such that transmission conditions are changed for each scanning line, thereby so as to form a uniform sound field in a scanning region. In the case where this invention is actually applied to a living body, it is desirable that transmission conditions be controlled while monitoring the sound field in a living body in consideration of design errors, tolerances, and a non-uniform medial quality or the like.

In this case, methods for monitoring a sound field include: a method for judging that a sound pressure is low at a dark site by referring to an image on a monitor (refer to FIG. 4) itself; and detecting the average intensity of the echo signals on each scanning line at the previously described sound field detecting section 26, and then, graphically displaying it as shown in FIG. 21. The average value used here may be obtained by each scanning line or among several scanning lines. Apart from the average value, an integral value, a maximum value, a minimum, value, or a median value and the like may be displayed. These values may be displayed independently at each depth, and may be displayed as a single value by sampling one scanning line.

In addition, in the case of contrast echo, it is important to carry out the detection at a transmission sound pressure that does not have an effect on contrast medium. Thus, for example, a technique in a publicly known monitor mode or the like is applicable. Further, in order to detect a transmission sound field at a low sound pressure, thereby achieving a contrast enhancement effect, in general, it is important to set transmission conditions when transmission at a high sound pressure is carried out. Of course, it is possible to set transmission conditions in advance prior to injection of a contrast medium.

Further, as shown in FIG. 21, the thresholds of the sound pressure or the like when a sufficient contrast enhancement effect can be achieved are displayed to be weighted or is displayed by coloring, whereby important information is easily identified in transmission condition setting, which is more effective. The display may be placed on a monitor and an operating panel or anywhere as long as it can be easily identified.

In the present embodiment, although there is provided a configuration such that transmission conditions are automatically controlled by the transmission control section so that a transmission sound field is almost equal in order to correct non-uniformity of image quality primarily produced due to a sector scan, the present invention is not always limited to such configuration. In the case where non-uniformity cannot be sufficiently corrected merely by making a transmission sound field almost uniform, for example, in the case of correcting non-uniformity of an image quality caused by the lungs or ribs and the like in a living body, there can be provided a configuration such that an operator can set transmission conditions by manual operation. In this case, for example, as shown in FIG. 22, it is desirable that an operating device operable by the operator such as dial/lever for sound pressure setting/aperture setting be provided at an operating section 14 for each of the scanning lines B1 to Bn or that scanning conditions for a plurality of scanning lines be set by one dial/lever because it is hard to adjust all the scanning lines. In this manner, transmission conditions can be arbitrarily changed by manual operation in consideration of a positional relationship of the lungs and ribs or the like in a living body. Thus, there is provided an advantage that the non-uniformity of images caused by these lungs and ribs can be effectively restrained.

In addition, in the case of contrast echo carried out by using a contrast medium, for example, a selector such as a selection button or the like capable of selecting type of contrast medium (levovist, optison, sonosoid or the like) is provided, making it possible to automatically set transmission conditions such as sound pressure according to the contrast medium selected by this selector.

In addition, in the case where uniformity cannot be obtained under transmission conditions because of device restriction or the like, the receiving conditions are changed, thereby making compensation for these transmission conditions. That is, in the case where non-uniformity cannot be corrected only under the transmission conditions, such non-uniformity is corrected by adjustment of the receiving conditions such as receiving gain. At this time, a configuration can be provided so as to properly change a correction quantity according to mode type (such as THI or contrast echo) or according to type of contrast medium (levobist, optison, sonasoid or the like) in the case of contrast echo. Namely, cases where non-uniformity cannot be corrected only under the transmission conditions include: a case where an aperture area for transmission beams on a scanning line with a large deflection angle is corrected so as to be larger than that of transmission beams on a scanning line with a small deflection angle; or a case where there is a need to make correction in excess of restriction on transmission condition such as sound pressure or aperture area determined by hardware or software limit of the ultrasonic diagnosis apparatus to be used in the case where the sound pressure of transmission beams on a scanning line with a large deflection angle is corrected so as to be higher than that of transmission beams on a scanning line with a small deflection angle.

The present invention can be carried out by variously modifying it without being limited to the described embodiments.

What is claimed is:

1. An ultrasonic diagnosis apparatus, comprising:
   a transmission condition controller configured to set a transmission condition to be given to an ultrasonic beam radiated to scan a region of a subject to be diagnosed,
   the transmission condition including at least one transmission condition other than a transmission frequency of the ultrasonic beam and being controlled in amount according to a scanning direction of the ultrasonic beam during a scanning operation thereof for one frame of an ultrasonic image of the subject so that non-uniformity of a transmission sound field in the region is corrected;
   an ultrasonic transmitter configured to transmit the ultrasonic beam to the subject under the at least one transmission condition set by the transmission condition controller; and
   an image generator configured to obtain the ultrasonic image of the subject from an ultrasonic echo signal reflected from the subject in response to transmitting the ultrasonic beam to the subject.

2. The ultrasonic diagnosis apparatus according to claim 1, wherein the ultrasonic transmitter is configured to change the at least one transmission condition in one image mode set to the ultrasonic image.

3. The ultrasonic diagnosis apparatus according to claim 1, wherein the at least one transmission condition includes at least one of a condition concerning a transmission aperture, including at least one of a transmission aperture area, a transmission aperture position, a transmission aperture shape, and a transmission aperture weighting function; and a transmission sound pressure.

4. The ultrasonic diagnosis apparatus according to claim 1, wherein the transmission condition controller is configured to set a transmission sound pressure or an MI (Mechanical Index) value in the region to be uniform or set a transmission sound pressure or an MI value in a virtual plane vertical to the scanning line to be uniform.

5. The ultrasonic diagnosis apparatus according to claim 1, wherein the image generator comprises a measure representing an index concerning the transmission sound field in each scanning direction using the ultrasonic echo signal.

6. The ultrasonic diagnosis apparatus according to claim 5, wherein the image generator comprises a display configured to display the index.

7. The ultrasonic diagnosis apparatus according to claim 5, wherein the transmission condition controller comprises a controller configured to control the transmission condition based on the index.

8. The ultrasonic diagnosis apparatus according to claim 1, wherein the transmission condition controller comprises a controller to enable an operator to manually control the at least one transmission condition.

9. The ultrasonic diagnosis apparatus according to claim 1, wherein the ultrasonic transmitter comprises a plurality of pulsars smaller in number a plurality of transmission scanning lines each of which is oriented in each scanning direction along which the ultrasonic beam is radiated respectively and a controller configured to switch the plurality of pulsars so that the ultrasonic beam is transmitted to the subject under the at least one transmission condition.

10. The ultrasonic diagnosis apparatus according to claim 1, wherein the image generator includes a controller configured to control a receiving condition for the ultrasonic echo signal in every scanning direction.

11. The ultrasonic diagnosis apparatus according to claim 1, wherein the transmission condition controller comprises:
    a selector configured to select a type of contrast medium to be injected into the subject; and
    a controller configured to control the at least one transmission condition according to the type of contrast medium selected by the selector.

12. The ultrasonic diagnosis apparatus according to claim 1, wherein the transmission condition controller is configured to set and control the at least one transmission condition depending on each scanning direction along which the ultrasonic beam is radiated to form the region to be scanned.

13. The ultrasonic diagnosis apparatus according to claim 1, wherein the transmission condition controller is configured to set and control the at least one transmission condition depending on every sub-region formed by dividing the region, each sub-region including one or more scanning directions along which the ultrasonic beam is radiated to form the region to be scanned.

14. An ultrasonic diagnosis apparatus, comprising:
    a transmission condition controller configured to set a transmission condition to be given to an ultrasonic beam radiated to scan a region of a subject to be diagnosed,
    the transmission condition including at least one transmission condition other than a transmission frequency of the ultrasonic beam and being controlled in amount according to a scanning direction of the ultrasonic beam during a scanning operation thereof for one frame of an ultrasonic image of the subject so that non-uniformity of a transmission sound field in the region is corrected;
    an ultrasonic transmitter configured to transmit the ultrasonic beam to the subject under the at least one transmission condition set by the transmission condition controller; and
    an image generator configured to sample a harmonics component from an ultrasonic echo signal reflected from the subject in response to transmitting the ultrasonic beam to the subject, thereby obtaining, as the ultrasonic image, a harmonic ultrasonic image of the subject from the harmonics component.

15. An ultrasonic diagnosis apparatus, comprising:
    a transmission condition controller configured to set, according to an operator's command, a transmission condition to be given to an ultrasonic beam radiated to scan a region of a subject to be diagnosed,
    the transmission condition including at least one transmission condition other than a transmission frequency of the ultrasonic beam and being controlled in amount according to a scanning direction of the ultrasonic beam during a scanning operation thereof for one frame of an ultrasonic image of the subject so that a transmission sound field in the region is entered into a desired state concerning the transmission sound field;
    an ultrasonic transmitter configured to transmit the ultrasonic beam to the subject under the at least one transmission condition set by the transmission condition controller; and
    an image generator configured to obtain the ultrasonic image of the subject from an ultrasonic echo signal reflected from the subject in response to transmitting the ultrasonic beam to the subject.

16. An ultrasonic diagnosis apparatus, comprising:
    a transmission condition controller configured to set a transmission condition to be given to an ultrasonic beam radiated to scan a region of a subject to be diagnosed,
    the transmission condition including at least one transmission condition other than a transmission frequency of the ultrasonic beam and being controlled in amount according to a scanning direction of the ultrasonic beam during a scanning operation thereof for one frame of an ultrasonic image of the subject so that non-uniformity of a transmission sound field in the region is corrected;
    a receiving condition corrector configured to correct a receiving condition for an ultrasonic echo signal reflected from the subject according to the at least one transmission condition set by the transmission condition controller;
    an ultrasonic transmitter configured to transmit the ultrasonic beam to the subject under the at least one transmission condition set by the transmission condition controller; and
    an image generator configured to process the ultrasonic echo signal into the ultrasonic image of the subject under the receiving condition corrected by the receiving condition corrector.

\* \* \* \* \*